United States Patent
Nelson et al.

(10) Patent No.: US 10,828,505 B2
(45) Date of Patent: Nov. 10, 2020

(54) THERAPEUTIC LIGHT SOURCE AND HANGING APPARATUS

(71) Applicant: Joovv, Inc., Crystal, MN (US)

(72) Inventors: Scott Nelson, Plymouth, MN (US); Justin Strahan, Crystal, MN (US)

(73) Assignee: Joovv, Inc., San Clemente, CA (US)

( * ) Notice: Subject to any disclaimer, the term of this patent is extended or adjusted under 35 U.S.C. 154(b) by 37 days.

(21) Appl. No.: 15/616,028

(22) Filed: Jun. 7, 2017

(65) Prior Publication Data

US 2018/0236259 A1 Aug. 23, 2018

Related U.S. Application Data (60) Provisional application No. 62/460,113, filed on Feb. 17, 2017.

(51) Int. Cl.
*A61N 5/06* (2006.01)

(52) U.S. Cl.
CPC .......... *A61N 5/0616* (2013.01); *A61N 5/0613* (2013.01); *A61N 2005/0642* (2013.01); *A61N 2005/0652* (2013.01); *A61N 2005/0659* (2013.01); *A61N 2005/0662* (2013.01)

(58) Field of Classification Search
None
See application file for complete search history.

(56) References Cited

U.S. PATENT DOCUMENTS

| | | |
|---|---|---|
| 6,626,932 B2 | 9/2003 | Whitehurst |
| 8,481,982 B2 | 7/2013 | Johnson et al. |
| 9,227,082 B2 * | 1/2016 | McDaniel ............ A61B 18/203 |
| 2004/0008523 A1 * | 1/2004 | Butler .................. A61N 5/0613 362/551 |
| 2009/0288340 A1 | 11/2009 | Hess |
| 2010/0309659 A1 | 12/2010 | Jenny |
| 2012/0104977 A1 | 5/2012 | Mckenzie |

(Continued)

OTHER PUBLICATIONS

Kind LED Grow Lights, "K5 Series Instructions", https://www.kindledgrowlights.com/pages/k5-setup, viewed Oct. 1, 2018, 2016.*

(Continued)

*Primary Examiner* — Christopher Koharski
*Assistant Examiner* — James Moss (57) ABSTRACT

A therapy lighting assembly, comprising a hollow housing, wherein a first surface has a plurality of openings, and the first side and the second side have a plurality of slots, a plurality of light emitting diodes (LED) arranged in predetermined arrays secured within the hollow housing so that the plurality of LEDs are substantially aligned with the plurality of openings, a plurality of attachment means secured to the first end of the hollow housing, and a positioning system comprising a plurality of attachment members, wherein the plurality of attachment members are detachably engaged with the plurality of attachment means, a connection means attached to the plurality of attachment members, a winching system integrated with the connection means, wherein the winching system adjusts the height of the hollow housing, and a mounting system connected to the winching system to secure the positioning system and the hollow housing.

1 Claim, 6 Drawing Sheets

(56) References Cited

U.S. PATENT DOCUMENTS

2015/0307332 A1* 10/2015 Huang .................... B66D 1/28
                                                      254/323
2018/0056087 A1*  3/2018 Ribeiro ............. A61F 13/00068

OTHER PUBLICATIONS

Mouser Electronics, "Enclosures and Racks", http://www.mouser.com/catalog/catalogusd/648/dload/pdf/ENCLOSECTION.pdf, from 2015, viewed on Oct. 4, 2018.*

"Kind LED Grow Lights K5 Series—Voted Best LED Grow Lights of 2014!", https://www.youtube.com/watch?v=NQDWBXIMxrk, posted Oct. 24, 2014, viewed on Oct. 2, 2018.*

WrethaOffGrid, "Ohuhu Pair of 1/8" Grow Light Rope Hanger review, https://www.youtube.com/watch?v=gYCsNQ9LELM, Sep. 29, 2016, viewed Oct. 5, 2018.*

OXO, "OXO Over The Door Hooks & Rack", https://www.youtube.com/watch?v=1WziS-a7LMI, Feb. 11, 2014, viewed Oct. 5, 2018.*

Woodworkers Store, "Swivel Mirror Screw", http://go.rockler.com/tech/Swivel-Mirror-Screws-Instructions.pdf, 1990, viewed Oct. 4, 2018.*

Kind LED, "K5 Series XL1000 Indoor LED Grow Light", https://www.kindledgrowlights.com/products/k5-xl1000, viewed on Oct. 4, 2018.*

Creative Fish Studio, "Ekostore 6 Watt Multi-color 36 LED Aquarium Light for 5 gallon tank", posted May 13, 2016, https://www.youtube.com/watch?v=s4FcYd81Pbw, viewed on Mar. 4, 2019.*

300W Full Spectrum Led Grow Lights 85-265V 5730SMD USA/DE/AU/CA Stock Hanging Kit For Plants Veg Hydroponics Grow Led.

* cited by examiner

THERAPEUTIC LIGHT SOURCE AND HANGING APPARATUS

BACKGROUND OF THE INVENTION

The present invention relates to a light source for use in therapy, and more particularly for treating a large external surface of a patient with an easy to use hanging apparatus so the light source is adjustable.

Specifically, red light therapy (RLT) involves having red or near infrared (NIR) light wavelengths emitted directly through the skin. Red or NIR light can be absorbed into the skin to a depth of about eight to 10 millimeters, at which point it has positive effects on cellular energy and multiple nervous system and metabolic processes.

Red light therapy has shown promise for treating symptoms of joint pain or osteoarthritis due to aging, those caused by cancer treatments like chemotherapy or radiation, hair loss, wounds or incisions, acne, wrinkles and skin discoloration, chronic muscular pain, neurological damage, and tissue damage (often at the root of tears, sprains or pulls).

Many of the current light therapy devices and lighting arrays are designed for desktop use or are complete chambers which the user enters. The vast majority of RLT devices on the market are either hand-held (very small treatment area) or a countertop unit that treats the face. Tanning salons offer red light treatment sessions in converted tanning beds using fluorescent circuits but the cost and size make these devices impractical for home use. In addition, the fluorescent circuits are very inefficient so the intensity of the light compromises the effectiveness of these devices.

Therefore, what is needed and heretofore lacking in prior light therapy solutions is a lighting apparatus that can be easily adjusted to the desired height of the user to expose the desired area to the red-light therapy.

SUMMARY

According to one aspect of the present invention, a therapy lighting assembly, comprising a hollow housing having a first surface, a second surface, a first side, a second side, and a first end, wherein the first surface has a first plurality of openings, the second surface has a second plurality of openings, and the first side and the second side have a plurality of slots, a plurality of light emitting diodes (LED) arranged in predetermined arrays secured within the hollow housing so that the plurality of LEDs are substantially aligned with the plurality of openings, a plurality of attachment means secured to the first end of the hollow housing, and a positioning system comprising of a plurality of attachment members, wherein the plurality of attachment members are detachably engaged with the plurality of attachment means, a connection means attached to the plurality of attachment members, a winching system integrated with the connection means, wherein the winching system adjusts the height of the hollow housing, and a mounting system connected to the winching system to secure the positioning system and the hollow housing.

According to another aspect of the present invention, a therapy lighting assembly, comprising a hollow housing, a hollow extruded core having a first surface, a first open end and a second open end and a plurality of openings are arranged on the first surface, a first end plate having a plurality of slots attached to the first open end of the hollow extruded core, a second end plate having a plurality of slots attached to the first open end of the hollow extruded core, a plurality of light emitting diodes (LED) encapsulated in an enclosure with a lens, wherein the lens directs the light emitted from the LED in a predetermined direction, and the plurality of LEDs are arranged in predetermined arrays secured within the hollow housing so that the plurality of LEDs are substantially aligned with the plurality of openings on the first surface of the hollow extruded core, a control panel attached to the hollow housing, wherein the control panel controls the plurality of LEDs, a positioning system comprising of a plurality of attachment members, wherein the plurality of attachment members are detachably engaged with the plurality of attachment means, a connection means attached to the plurality of attachment members, a winching system integrated with the connection means, wherein the winching system adjusts the height of the hollow housing, and a mounting system connected to the winching system to secure the positioning system and the hollow housing, and an electrical system providing adequate power to the therapy lighting assembly.

According to yet another aspect of the present invention, a therapy lighting assembly, comprising a plurality of light emitting diodes (LED) arranged in a predetermined array within a housing, wherein the housing has a top surface, a plurality of threaded posts attached to the top surface of the housing, a plurality of threaded caps designed to detachably engage the threaded posts, a plurality of cables, wherein each of the plurality of cables are attached to one of the plurality of thread caps at a first end and the second end of the cable is looped, a releasable shackle inserted through the loops of the plurality of cables, a rope inserted through the releasable shackle, wherein the rope passes through a ratcheting pulley; and a hook having a protrusion, wherein the ratcheting pulley releasably engages with the protraction of the hook.

DETAILED DESCRIPTION OF THE INVENTION

The present invention describes a light emitting diode (LED) red light display (RLD) device. The RLD is designed to hang on a door or solid structure to allow for easy use and convenient storage. The height of the RLD is also adjustable to allow for adjustments on the area of the user's body which is exposed to the LEDs. Major advantages of the RLD is the large treatment area, the adjustable height, compact design, and easy method of installing the RLD.

As will be apparent to those of skill in the art upon reading this disclosure, each of the individual embodiments described and illustrated herein has discrete components and features which may be readily separated from or combined with the features of any of the other embodiments without departing from the scope or spirit of the present invention. It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein may also be used in the practice or testing of the present invention, the preferred methods and materials are now described.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Figure 1:
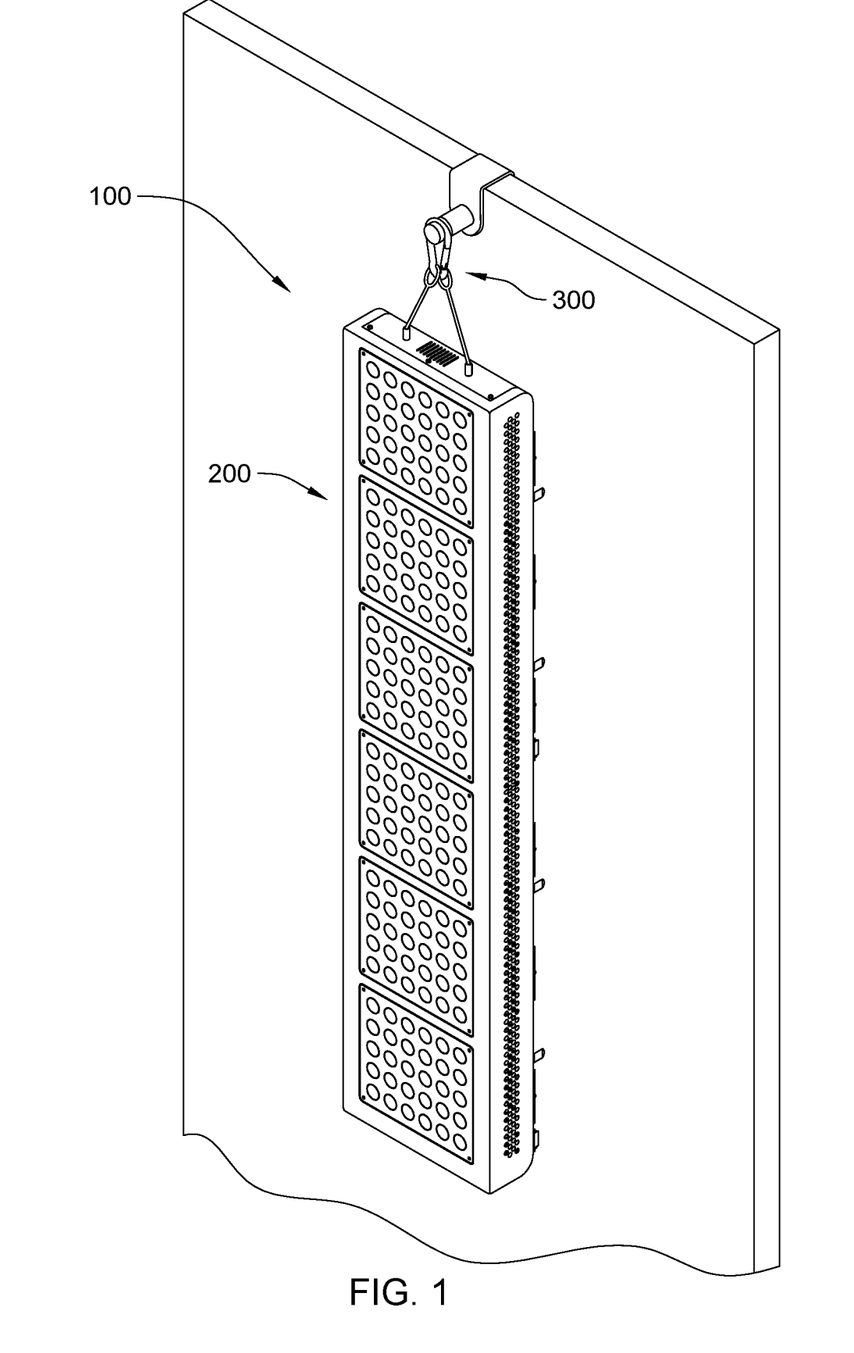
FIG. 1 depicts an isometric view of a hanging therapy light assembly, in accordance with one embodiment of the present invention.

FIG. 1 depicts an isometric view of a hanging therapy light assembly, 100, in accordance with one embodiment of the present invention. The hanging therapy light assembly 100 is comprised of a therapy light enclosure 200 and a positioning system 300. The hanging therapy light assembly 100 allows a user to experience the benefits of a professional therapy light setup in a smaller structure, that is easily customizable to direct the effects of the therapy lights on to the specific areas of the user's body and also allow the user the comfort of experiencing the benefits of the therapy lights in the comfort of their own home.

In the depicted embodiment, the therapy light enclosure 200 is hung from a door via the mounting system 300. The therapy light enclosure 200 is depicted with five (5) light panels in a single column. In additional embodiments, the therapy light enclosure 200 may have more or less light panels, and may have more than one (1) column of light panels.

Figure 2:
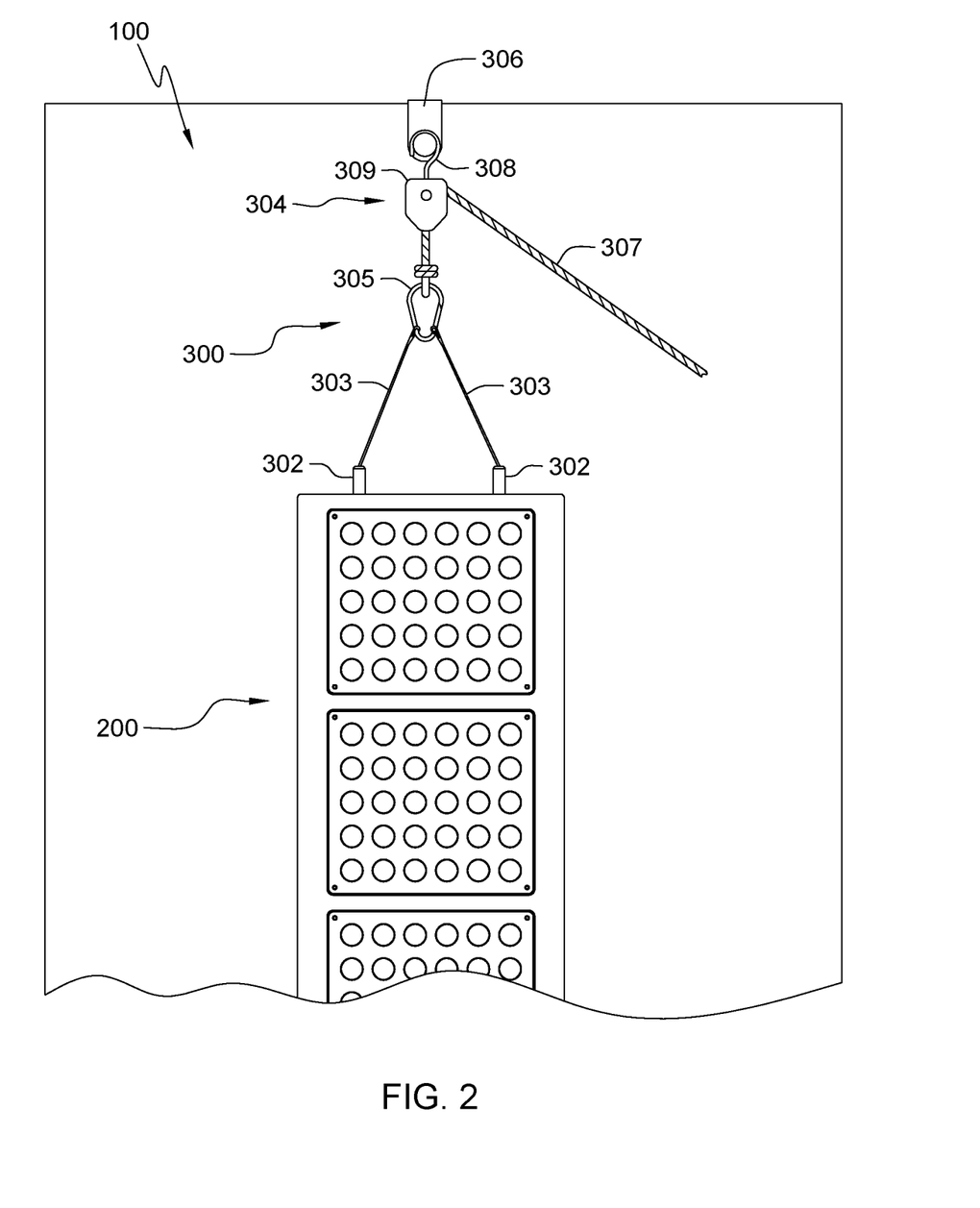
FIG. 2 depicts a front view of a therapy light enclosure and a positioning system, in accordance with one embodiment of the present invention.

FIG. 2 depicts a front view of the upper portion of the therapy light enclosure 200 and the positioning system 300, in accordance with one embodiment of the present invention. The positioning system 300 is comprised of an attachment means 302, a suspension system 304, and a mounting member 306. The positioning system 300 provides the benefits of allowing the user to customize the height and position of the therapy light enclosure 200, the positioning system 300 allows the user to easily raise, lower, or rotate the therapy light enclosure 200 to the desired position. As well as allow the user to easily install and remove the therapy light enclosure 200.

The attachment means 302 is designed to detachably engage with an anchor member on the therapy light enclosure 200 that is connected to the positioning system 300 securing the therapy light enclosure 200 with the positioning system 300. In the depicted embodiment, the attachment means 302 is a cap with a threaded internal compartment that is designed to mate with an anchor member on the therapy light enclosure with a reciprocal thread. A cord 303 is attached to each attachment means 302 and is connected to a detachable fastener 305. The cord 303 may be made from various materials provided they are able to support the weight of the therapy light enclosure 200. The length of the cords 303 is predetermined to provide a substantially level and secure position. The detachable fastener 305 is designed to allow the user to connect and disconnect the cords 303 from the positioning system 304 with ease. In the depicted embodiment, the detachable fastener 305 is a carabiner. In additional embodiments, the detachable fastener 305 may be various clips, clasps, hooks, latches or the like that are detachable.

The positioning system 304 allows the user to position the therapy light enclosure 200 at a desired height or position. In the depicted embodiment, the positioning system 304 is a pulley 309 with a cable 307 threaded through the pulley 309 and attached to the detachable fastener 305. The pulley 309 may be, but not limited, various pulleys that are self-locking, ratchet style pulleys, or the pulleys that allow a user to lock or hold the therapy light enclosure 200 in place without the user's assistance. In one embodiment, the pulley 309 has a lever which disengages the locking system so that the user can easily lower the therapy light enclosure 200. In additional embodiments, the lever or disengagement member may be various designs or structures known to those in the art. In some embodiments, the pulley 309 is motorized allowing an electronically or mechanically controlled raising and lowering of the therapy light enclosure 200.

The cable 307 is of a predetermined length to allow a user to easily access the cable 307 to pull the therapy light enclosure 200 to a desired height/position. The cable 307 is made from a material such as steel, aluminum, copper, or fabrics that are able to support the therapy light enclosure 200. In the depicted embodiment, the pulley 309 is connected to a hook 308. The hook 308 provides the necessary attachment means to connect the therapy light enclosure 200 to the mounting member 306. In various other embodiments, other styles of locking pulleys may be used, as well as a pulley that does not lock but the user can tie down the cord to keep the therapy light enclosure 200 in a desired position or height.

The mounting member 306 is designed to secure the therapy light enclosure 200 to a door, wall, or other structural surface in which the user desires to mount the therapy light enclosure 200 to. In the depicted embodiment, the mounting member 306 is a custom made, over-the-door hook for which the pulley system 304 is attached to via hook 308. The over-the-door hook allows for easy installation and removal on a door or door-like structure. In additional embodiments, various types of mounting systems may be used that are both removable or permanent that are known to those skilled in the art. In additional embodiments, the mounting member 306 may be a freestanding hanging system.

Figure 3:
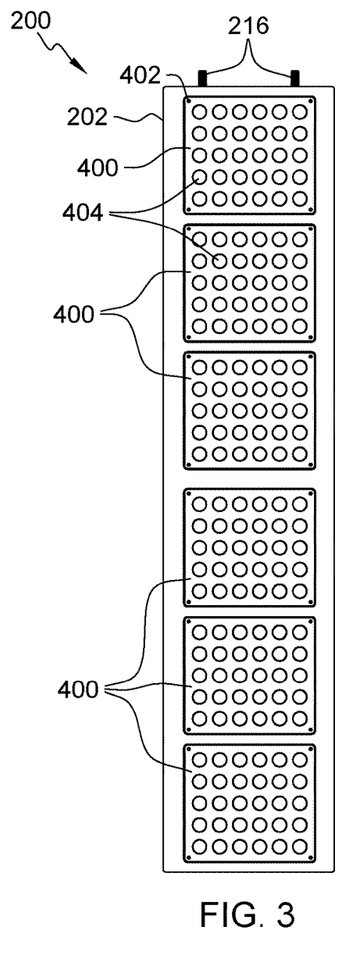
FIG. 3 depicts a front view of the therapy light enclosure, in accordance with one embodiment of the present invention.

FIG. 3 depicts a front view of the therapy light enclosure 200, in accordance with one embodiment of the present invention. In the depicted view, the therapy light enclosure 200 is comprised of the housing 202 and six (6) rows of the therapy light diodes 400. In additional embodiments, there may be more or less rows of therapy light diodes 400 and more than one column of therapy light panels 400.

The housing 202 contains and protects the sensitive elements of therapy light panel(s) 400 and the associated electrical components. In the depicted embodiment, the housing 202 has a plurality of openings sized to receive the therapy light panel(s) 400. The therapy light panel(s) 400 are secured in place with fasteners 402 or various other attachment means, such as, but not limited to, pressure clips, bolts, screws, clips, clamps, or the like. In the depicted embodiment, the housing 202 is a substantially rectangular design. In additional embodiments, the housing 202 may have a square, circular, or other shape dependent upon the intended area or portion of the user's body that is to be affected by the therapy light panels 400. In additional embodiments, the housing 202 may have a modular design, wherein therapy light panels 400 or therapy light enclosures 200 may be attached and detached, and the housing 202 may be made from, but not limited to aluminum, steel, iron, copper, brass, bronze, zinc, stainless steel, or the like.

In the depicted embodiment, the attachment members 216 are shown on the top surface of the housing 202. The attachment members 216 are positioned a predetermined distance from the outer edges of the housing 202 to provide a stable and level design. The attachment members 216 may be integrated into the housing 202 or may be detachable to allow for easy replacement based on the type of attachment means 302 used in the positioning system 300.

The therapy light panel 400 provides the therapeutic light within the desired wavelength to the user. The therapy light panel 400 is comprised of a plurality of LED circuits 404 designed to produce the specific and predetermined wavelengths of light. The light is within a band of red and infrared wavelengths. It is this bandwidth of the LED circuits 404 in the red and infrared portion of spectrum that allows the body's inflammation response to be activated in cells near to the skin surface without damaging the skin, thereby enabling non-ablative skin rejuvenation phototherapy to occur, i.e., the body's natural wound healing process may be trigged even though no actual damage has been incurred.

In one embodiment, all of the LED circuits 404 in the therapy light panel 400 have a mid spectrum wavelength of about 660 nm, i.e., red, half maximum (FWHM) wavelength range that extends from about 600 nm to about 700 nm. In another embodiment, all of the LED circuits 404 have a light spectrum emitted by a band of infrared LED circuits with a mid spectrum wavelength of about 850 nm, i.e., infra-red, half maximum (FWHM) wavelength range that extends from about 700 nm to about 900 nm. In additional embodiments, the LED circuits 404 within the therapy light panel 400 may be mixed between the 630 nm and the 850 nm. It is the narrow bandwidth of the LED circuits within the red and infrared portion of spectrum that allows the cells to increase ATP production and, thereby, their metabolism, and so aid the rejuvenation process. In additional embodiments, the LED circuits 404 wavelength may be extended beyond the limits listed above, provided the wavelength still provides the same ATP production and healing benefits. In additional embodiments, the wavelength produced by the LED circuits 404 may be approximately 1050 nm or infrared light. In additional embodiments, the wavelength produced by the LED circuits 404 may be approximately 530 nm.

The LED circuits 404 are arranged in predetermined arrays. The purpose of the array is to create a structure of LED circuits 404 that produce the desired light at a predetermined concentration and coverage area, from a predetermined distance. In one embodiment, the LED circuits 404 are positioned within the therapy light panels 400 so that the light is projected in a substantially straight direction. In additional embodiments, the LED circuits 404 may be angled within the therapy light panels 400 to direct the light in a predetermined direction.

In the depicted embodiment, the LED circuits are positioned in a square array. In additional embodiments, various array patterns may be used, such, but not limited to rectangular, circular, hexagonal, and the like. In one embodiment, the therapy light panels 400 are designed to produce $$\frac{4 \text{ joules}}{17 \text{ mW/cm2}}$$

from a distance of approximately twelve (12) inches. Each panel covers approximately an eighteen (18) inches by fourteen (14) inches area of the user's body. Thus, in one embodiment, the user needs exposure for approximately four (4) minutes to receive the desired results from the therapy light panel 400.

In the depicted embodiment, each LED circuit 404 is placed within a specialized chamber and receded a predetermined distance from the surface of the therapy light panel 400 to concentrate the light produced from the LED circuit 404 in a predetermined direction and intensity. In one embodiment, each LED circuit 404 chamber has a clear lens to protect the LED circuit 404 from debris or damage. In some embodiments, the lens has a predetermined density and curvature to produce refraction of the light, thereby directing the light emitted from the LED circuit 404 at a predetermined angle. This refraction assists in achieving the substantially complete coverage of the user's body when they are positioned using the predetermined distance from the therapy light panel 400. In one embodiment, the lenses refract the light at sixty (60) degrees. In additional embodiments, the lenses refract the light at, ninety (90), one hundred and twenty (120), or various other degrees.

Figure 4:
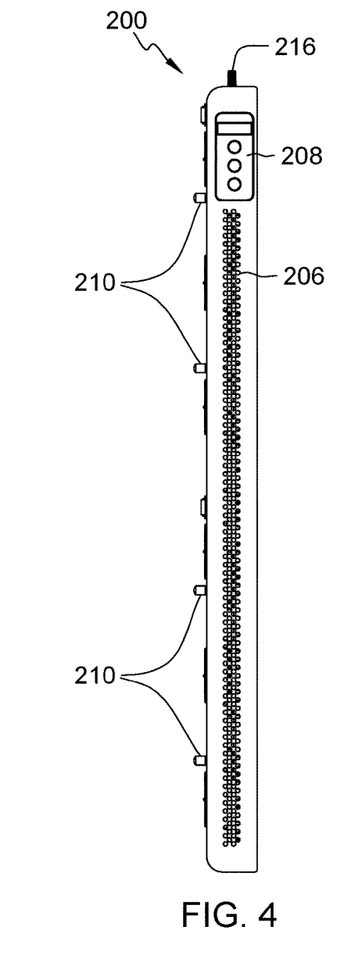
FIG. 4 depicts a side view of the therapy light enclosure, in accordance with one embodiment of the present invention.

FIG. 4 depicts a side view of the therapy light enclosure 200, in accordance with one embodiment of the present invention. The side of the therapy light enclosure 200 has a plurality of ventilation openings 206 to improve air flow within, into, and out of the housing 202. In the depicted embodiment, the ventilation openings 206 are small circular openings cover a predetermined section of the side of the housing 202. In additional embodiments, the ventilation openings 206 may be slots or openings of various other shapes. In additional embodiments, the portion of the side of the housing 202 which has the ventilation openings 206 may be adjusted based on the required airflow.

In the depicted embodiment, the side of the therapy light enclosure 200 has a control panel 208 that is used to control the various functions of the hanging therapy light apparatus 100. The control panel 208 may be used for, but not limited to turning on the therapy light panels 300, turning on the fans 500, setting a timer for the therapy light panels 400 or the fans 500 are active for, or the like. In some embodiments, the control panel 208 may be used to raise and lower the therapy light enclosure 200 if the mounting system 300 is motorized. In some embodiments, the control panel 208 may be controlled by wireless technology such as, for example, Bluetooth® or other near field communication systems. In additional embodiments, the control panel 208 may be placed in various locations on the therapy light enclosure 202 provided the control panel 208 is easily accessible and does not interfere with the therapy light functionality.

In the depicted embodiment, a plurality of bumpers 210 disposed on the rear side of the therapy light enclosure 200 to offset the therapy light enclosure 200 from a surface. This assists in providing excess airflow behind the therapy light enclosure to provide adequate air flow within and around the therapy light enclosure 200. The bumpers 210 are made of an elastic material such as rubber to assist in absorbing shock as well. The bumpers 210 may be made of various other materials known to those skilled in the art.

Figure 5:
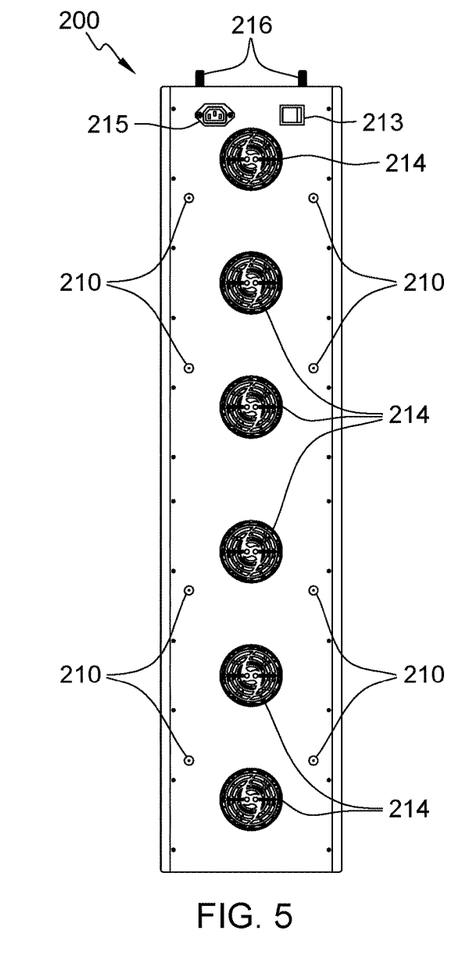
FIG. 5 depicts a rear view of the therapy light enclosure, in accordance with one embodiment of the present invention.
Figure 6:
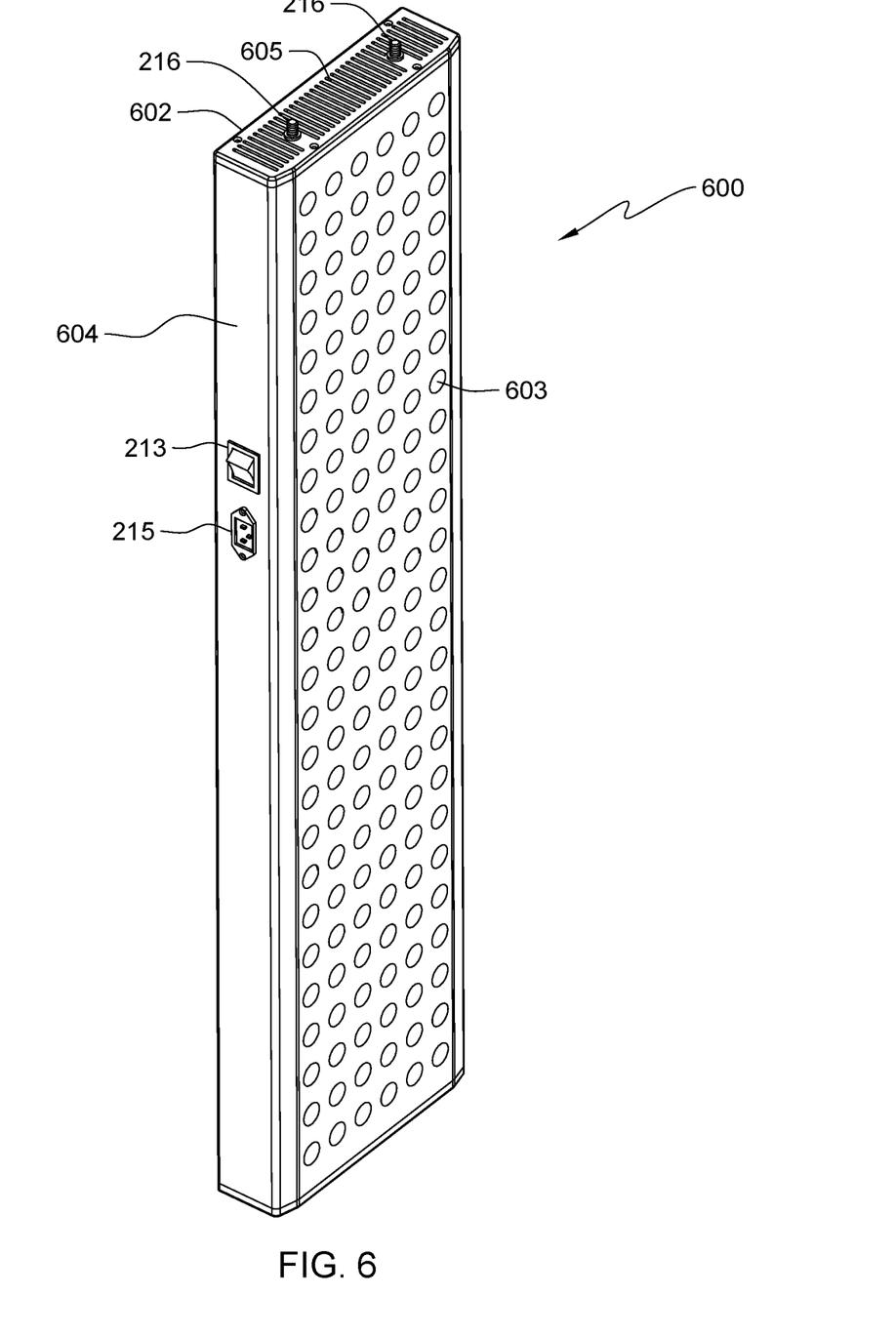
FIG. 6 depicts an isometric view of a hanging therapy light assembly, in accordance with another embodiment of the present invention.
Figure 7:
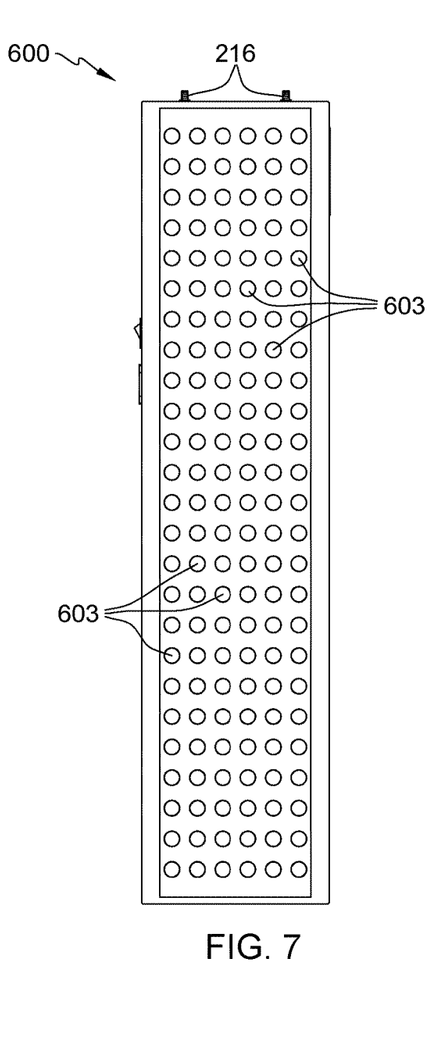
FIG. 7 depicts a front view of the therapy light enclosure, in accordance with another embodiment of the present invention.
Figure 8:
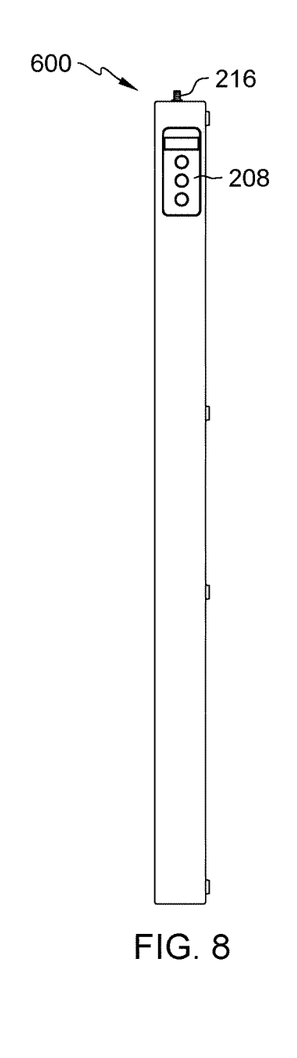
FIG. 8 depicts a side view of the therapy light enclosure, in accordance with another embodiment of the present invention.
Figure 9:
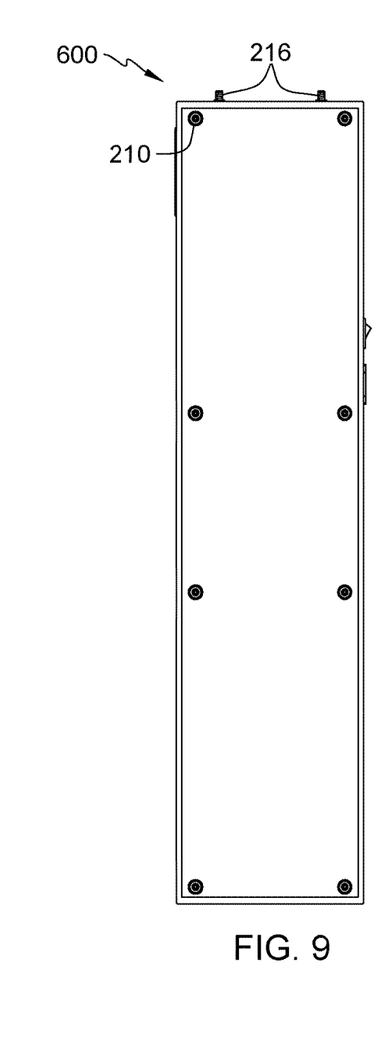
FIG. 9 depicts a rear view of the therapy light enclosure, in accordance with another embodiment of the present invention.

FIG. 5 depicts a rear view of the therapy light enclosure 200, in accordance with one embodiment of the present invention. The rear side of the therapy light enclosure 200 has a plurality of ventilation slots 214 to allow air to enter or exit the housing 202. In some embodiments, a fan is positioned near the ventilation slots 214 to assist in cooling the therapy light panels 400 and the electrical system. The plurality of ventilation slots 214 are positioned in predetermined locations that coincide with the positioning of the therapy light panels 400 and the electrical system. In the depicted embodiment, a plurality of bumpers 210 are positioned on the rear side of the housing 202 to assist in leveling the therapy light enclosure 200 against a surface. In the depicted embodiment, a power switch 213 and a power outlet 215 are shown.

FIGS. 6-9 depict an isometric view of a hanging therapy light enclosure 600, in accordance with another embodiment of the present invention. In the depicted embodiment, the hanging therapy light enclosure 600 has a central housing 604, a top plate 602, and a bottom plate 606. In this embodiment, the therapy light panels are enclosed entirely within the central housing, and the LED circuits align with the openings 603. The top plate 602 is secured to the central housing 604 and has a plurality of slots 605 to allow for air to enter and/or exit the interior of the central housing 604. In one embodiment, fans are secured to the top plate 602 to further increase the volume of air entering and/or exiting the interior compartment of the central housing 604. The top plate 602 has attachment members 216 to connect to the positioning system 300. In one embodiment, the attachment members 216 and the top plate 604 are a unitary design. In the depicted embodiment, the power switch 213 and the power outlet 215 are located on the side of the central housing 604. In additional embodiments, the positioning of these elements may be in various locations. In many embodiments, the bottom plate 606 has similar slots to the slots 605 in the top plate 604 to allow air flow throughout the entire central housing 604. The rear side of the central housing 604 has bumpers 210. In the depicted embodiments, the rear side of the central housing 604 is removable to allow access to the internal components. In additional embodiments, the central housing 604 is a solid unitary design in which the internal components are inserted through the top or bottom and secured once inserted.

Figure 10:
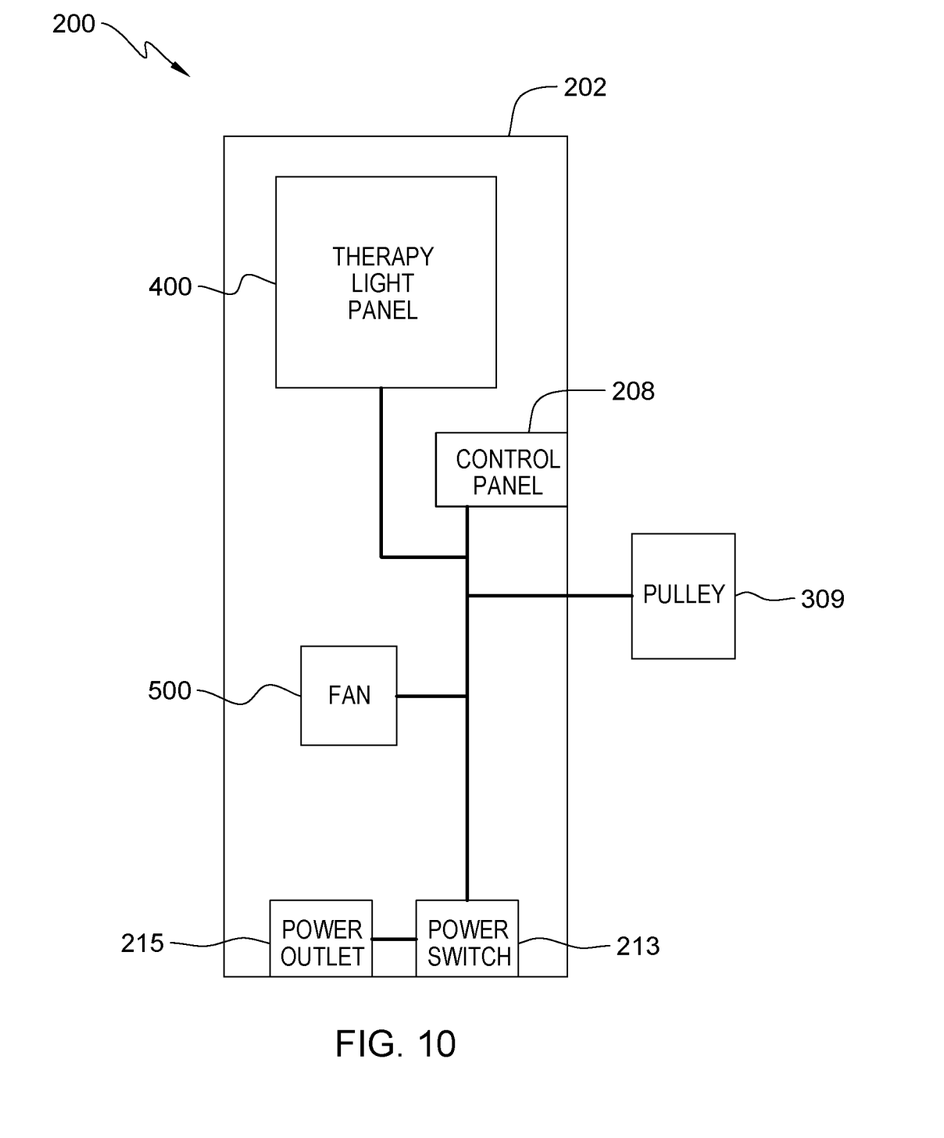
FIG. 10 depicts a schematic view of the electrical components of the therapy light assembly, in accordance with one embodiment of the present invention.

FIG. 10 depicts a block diagram of the electrical components of the therapy light assembly 100, in accordance with one embodiment of the present invention. The electrical components of the depicted embodiment include, a power switch 213, a power outlet 215, at least one fan 500, the therapy light panel 400, the control panel 208, and the pulley 309 connected electronically to supply the necessary power to operate each element of the hanging therapy light assembly 100. Various electrical setups and structures are possible to those skilled in the arts.

A power supply is used to power the therapy light panel 400, the fans 500, the control panel 208, and the various other electrical components of the hanging therapy light apparatus 100. In the depicted embodiment, the power supply is a power outlet 215 exposed on the surface of the housing 202. In additional embodiments, the power supply may be an internal battery that is rechargeable and the power outlet 215 is used to recharge the battery.

In the depicted embodiment, the switch 213 is used to turn on or off the electronic elements of the hanging therapy light apparatus 100. In some embodiments, the switch is not required or is incorporated into the control panel 208.

The fans 500 are positioned in close proximity to the therapy light panels 300 to provide efficient and effective cooling. This may involve the fans 500 being mounted directly to the therapy light panels 300. The fans 500 may also be mounted directly to the housing 202. The fan 500 are located to be substantially in line with the therapy light panel 204 to provide the greatest amount of air flow over the therapy light panel 204 to remove the heat produced by the LED circuits and the electrical systems. In one embodiment, the fan may be a dual ball bearing, 120 mm, 0.10 A 12V cooling fan. In additional embodiments, the fan 500 may have various other sizes, speeds, power consumptions, and designs. In one embodiment, the fans 500 are able to switch directions so that the air flow can be modified. In one embodiment, the fans are attached to the therapy light enclosure 200. In another embodiment, the ventilation slots 214 are approximately the same size as the fans. In additional embodiments, the ventilation slots 214 may take on a variety of shapes to further assist in the ventilation of the internal compartment of the housing 202. In additional embodiments, the fans 500 are attached to the top plate 604, the bottom plate 606, or both. In some embodiments, fans 500 are located externally and directed at the user to provide a cooling feature for the user.

The control panel 208 is used to control the various settings and power options of the hanging therapy light assembly 100. The control panel 208 is located on the external surface of the therapy light enclosure 200, 600. The control panel 208 may control, but not limited to, the power of the therapy light panels 400, the time the therapy light panels 400 are active, the intensity of the therapy light panels 400, the speed of the fans 500, and the pulley 309 if the pulley is motorized. In various embodiments, the control panel 208 may control many of these features automatically or they may be controlled by the user.

The invention is inclusive of combinations of the embodiments or embodiments described herein. References to "a particular embodiment" or "embodiment" and the like refer to features that are present in at least one embodiment of the invention. Separate references to "an embodiment" or "particular embodiments" or "embodiments" or the like do not necessarily refer to the same embodiment or embodiments; however, such embodiments are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

While this invention has been described in conjunction with the specific embodiments outlined above, it is evident that many alternatives, modifications and variations will be apparent to those skilled in the art. Accordingly, the preferred embodiments of the invention, as set forth above, are intended to be illustrative, not limiting. Various changes may be made without departing from the spirit and scope of this invention. The present invention shall be easily carried out by an ordinary skilled person in the art, and any modifications and changes are deemed to be within the scope of the present invention.

This written description uses examples to disclose the invention, including the best mode, and also to enable any person skilled in the art to practice embodiments of the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

What is claimed is:

1. A light therapy system, comprising:
    a hollow housing having a first surface, a second surface parallel to the first surface and facing opposite the first surface, a first side extending perpendicular between the first surface and the second surface, a second side parallel to the first side and facing opposite the first side, and a first end extending perpendicular between the first surface, the second surface, the first side, and the second side, wherein the first surface has a first plurality of openings;
    a plurality of light emitting diodes (LEDs) coupled to the hollow housing and arranged in predetermined arrays secured within the hollow housing so that the plurality of LEDs are substantially aligned with the plurality of openings, wherein no LEDs of the plurality of LEDs emit light having a wavelength of less than at least 600 nm;
    a plurality of attachment posts coupled to the first end;
    a positioning system comprising:
        a plurality of attachment members detachably coupled to the plurality of attachment posts,
        a connection member coupled to the plurality of attachment members, and
        a winching system integrated with the connection member, wherein the winching system is arranged and configured to adjust a vertical position of the hollow housing,
    wherein the hollow housing is comprised of a hollow extruded core having a first open end and a second open end, a first end plate attached to the first open end, and a second end plate attached to the second open end, and
    wherein the first end plate has a plurality of slots positioned in predetermined locations and at least two openings arranged and configured to receive the plurality of attachment members.

* * * * *

(12) EX PARTE REEXAMINATION CERTIFICATE (11951st)
United States Patent
Nelson et al.

(10) Number: US 10,828,505 C1
(45) Certificate Issued: Dec. 1, 2021

(54) THERAPEUTIC LIGHT SOURCE AND HANGING APPARATUS

(71) Applicant: Joovv, Inc., Crystal, MN (US)

(72) Inventors: Scott Nelson, Plymouth, MN (US); Justin Strahan, Crystal, MN (US)

(73) Assignee: JOOVV, INC, San Clemente, CA (US)

Reexamination Request:
No. 90/014,849, Sep. 1, 2021

Reexamination Certificate for:
Patent No.: 10,828,505
Issued: Nov. 10, 2020
Appl. No.: 15/616,028
Filed: Jun. 7, 2017

Related U.S. Application Data (60) Provisional application No. 62/460,113, filed on Feb. 17, 2017.

(51) Int. Cl.
*A61N 5/06* (2006.01)
(52) U.S. Cl.
CPC .......... *A61N 5/0616* (2013.01); *A61N 5/0613* (2013.01); *A61N 2005/0642* (2013.01); *A61N 2005/0652* (2013.01); *A61N 2005/0659* (2013.01); *A61N 2005/0662* (2013.01)

(58) Field of Classification Search
CPC combination set(s) only.
See application file for complete search history.

(56) References Cited

To view the complete listing of prior art documents cited during the proceeding for Reexamination Control Number 90/014,849, please refer to the USPTO's public Patent Application Information Retrieval (PAIR) system under the Display References tab.

*Primary Examiner* — Beverly M Flanagan (57) ABSTRACT

A therapy lighting assembly, comprising a hollow housing, wherein a first surface has a plurality of openings, and the first side and the second side have a plurality of slots, a plurality of light emitting diodes (LED) arranged in predetermined arrays secured within the hollow housing so that the plurality of LEDs are substantially aligned with the plurality of openings, a plurality of attachment means secured to the first end of the hollow housing, and a positioning system comprising a plurality of attachment members, wherein the plurality of attachment members are detachably engaged with the plurality of attachment means, a connection means attached to the plurality of attachment members, a winching system integrated with the connection means, wherein the winching system adjusts the height of the hollow housing, and a mounting system connected to the winching system to secure the positioning system and the hollow housing.

EX PARTE REEXAMINATION CERTIFICATE

NO AMENDMENTS HAVE BEEN MADE TO THE PATENT

AS A RESULT OF REEXAMINATION, IT HAS BEEN DETERMINED THAT:

The patentability of claim 1 is confirmed.

\* \* \* \* \*